United States Patent
Ashworth et al.

[11] Patent Number: 5,393,820
[45] Date of Patent: Feb. 28, 1995

[54] FLAME RETARDANT COMPOUNDS AND COMPOSITIONS CONTAINING THEM

[75] Inventors: Paul Ashworth, Holywell; Michael J. Schneider, Chester, both of Great Britain

[73] Assignee: The Associated Octel Company Limited, London, United Kingdom

[21] Appl. No.: 934,432

[22] PCT Filed: Mar. 4, 1991

[86] PCT No.: PCT/GB91/00322
§ 371 Date: Nov. 3, 1992
§ 102(e) Date: Nov. 3, 1992

[87] PCT Pub. No.: WO91/13858
PCT Pub. Date: Sep. 19, 1991

[30] Foreign Application Priority Data
Mar. 5, 1990 [GB] United Kingdom ............... 9004857

[51] Int. Cl.⁶ .................. C08K 5/03; C08K 3/10; C07C 69/76

[52] U.S. Cl. .................. 524/466; 524/288; 524/296; 524/412; 560/83; 560/87

[58] Field of Search .......... 524/288, 296, 411, 469, 524/412, 466; 560/83, 87, 192, 197

[56] References Cited

U.S. PATENT DOCUMENTS
3,772,342 11/1973 Foley et al. .......... 560/83
4,376,837 3/1983 Jenkner et al. .......... 524/108

FOREIGN PATENT DOCUMENTS
8701713 3/1987 WIPO .
8803542 5/1988 WIPO .

*Primary Examiner*—Tae H. Yoon
*Attorney, Agent, or Firm*—Renner, Otto, Boisselle & Sklar

[57] ABSTRACT

Flame retardant polyesters are disclosed comprising esters of tribromoneopentyl alcohol with orthophthalic acid and its halogenated derivatives, particularly tetrabromo-orthophthalic acid an hydride.

5 Claims, No Drawings

FLAME RETARDANT COMPOUNDS AND COMPOSITIONS CONTAINING THEM

This invention relates to flame retardant compounds and compositions containing them.

Brominated organic compounds are well known to have flame retardant properties and are extensively used for this purpose in a wide variety of materials such as plastics and rubber, and including cellular and foamed materials such as foamed polystyrene and foamed polyurethanes.

The vapour phase mode of action of these compounds relies to a great extend on the thermal stability of the brominated compound in relation to that of the polymer. If the flame retardant compound has too low a thermal stability, i.e. begins to decompose or vaporise at too low a temperature, then it will be exhausted before the polymer itself starts decomposing. If the flame retardant has too high a thermal stability, it will remain in the condensed phase, and will therefore remain inactive as the polymer decomposes. Thus it is desirable to have a flame retardant compound whose thermal stability closely matches that of the polymer.

The thermal stability of various known flame retardants is given below, an accepted measure of thermal stability being the temperature in °C. at which there is a 10% loss in weight; ("Thermal Characteristics of Polymer Materials", E A Turi, Academic Press, 1981):

|  | 10% wt. loss at |
|---|---|
| decabromodiphenyloxide (DBDPO) | 373° C. |
| octabromodiphenyloxide (OBDPO) | 340° C. |
| bis (2-hydroxyethyl) ether of tetrabromobisphenol A | 337° C. |
| octabromodiphenyl | 336° C. |

Of these DBDPO has been extensively used as flame retardant in ABS (acrylonitrile-butadiene-styrene) rubbers and other similar engineering thermoplastics (ETP) that have a high thermal stability, e.g. high impact polystyrene (HIPS) and therefore require a high thermal stability flame retardant to match. ABS, for example, shows decomposition to 10% weight loss at about 390° C. (Stanton Redcroft STA 1000, 10° C. min.$^{-1}$ 30 ml.min$^{-1}$ air, sample weight 10±0.02 mg. Inconel crucible). This figure is reasonably closely matched by that of DBDPO at 373° C. However, the use of DBDPO has recently come into question, as it is suspected of forming highly toxic brominated dibenzodioxins and -furans upon pyrolsis, and these products have, indeed, been detected in the pyrolysis of polymer systems containing DBDPO.

Octabromodiphenyloxide has been substituted for DBDPO but is less effective as a flame retardant, and is also suspected of forming brominated dibenzo-dioxins and -furans upon pyrolysis.

In GB Patent No. 1341458, flame retardant benzene polycarboxylic esters of halogenated monohydric alcohols having a neopentyl-type configuration are disclosed, namely compounds of the formula.

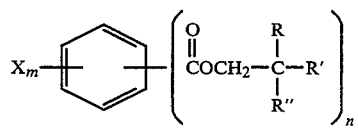

where R, $R^1$ and $R^2$ are halogenated methyl groups, X is halogen, n is 2 or 3, and m is 0–4, with the proviso that, when n is 2, the ester groups are in the meta or para-positions on the benzene ring, and when n is 3 (in which case m is correspondingly 0–3) the ester groups are in the 1, 3 and 5 positions. In other words, the compounds disclosed in GB1341458 are the halogenated neopentyl esters, especially the tribromoneopentyl esters of isophthalic acid, terephthalic acid and trimesic acid, and their halogenated derivatives.

In GB 1342458 attention is focused on esters, or iso- and terephthalic acid and of trimesic acid having aliphatic, rather than aromatic, halogenation, that is to say wherein the bromine or chlorine substituents are in the aliphatic side chains rather than in the aromatic ring. Aromatic substitution is embraced within the broad formula, but only one working example is given, namely the preparation of the compound di[2,2 bis(bromomethyl)-3-bromopropyl] tetrachloroterephthalate, or, in accordance with the trivial, rather than systematic, nomenclature used herein: bis-(tribromoneopentyl)tetrachloroterephthalate. There is no exemplification of any compounds having brominated aromatic rings.

The esters disclosed in GB 1341458 are indicated to have flame retardant properties, and to be useful as flame retardant additives in a wide range of synthetic plastics, inter alia hydrocarbon polymers such as polypropylene, polystyrene, styrene-butadiene rubber and butyl rubber, and non-hydrocarbon polymers, e.g. polyesters such as poly(ethylene terephthalate), polyurethanes, poly(alkylene oxides), ethylene-vinyl acetate copolymers, acrylic polymers and copolymers, epoxyresins, poly(vinyl chloride). Also included are references to butadiene-acrylonitrile and butadiene-acrylonitrile-styrene copolymers, but no such formulations appear to have been manufactured or tested.

The compounds of GB 1341458 are thus put forward as general weight based on the total weight of the composition in the case of chlorinated compounds, and from 1 to 15% by weight in the case of the brominated compounds, usually in combination with 1 to 15% by weight of an antimony compond such as antimony trioxide. The weight loss of the claimed compounds is said to be less than 5% at up to 300° C. but with values ranging from 1 to 34% at 350° C.

The preferred applications are indicated to be as flame retardants in homopolymers or random, block or graft copolymers of alpha-olefins of 2 to 6 carbon atoms, polystyrene, polyurethane, polyamides and polyesters.

Various other tetrahalophthalate esters are known and have been proposed as flame retardant additives, particularly for polypheylene other resins. Reference may be made in this respect to WO 88/03542 which mentions the use inter alia of alkyl diesters of tetrabromophthalic acid for this purpose, and including a broad reference also to $C_2$14 $C_4$ haloalkyl esters of tetrabromophthalic acid, although no specific examples are given. The preferred compounds are the alkyl diesters specifically di-(2-hydroxypropyl methoxy polyoxyethylene glycol) ester of tetrabromophthalic acid.

Compounds of a similar structure are to be found in WO 87/01713 which discloses flame retardant tetrabromo- and tetrachloro-phthalate esters comprising the mono-, di- and polyesters of tetrabromo- and tetrachloro-phthalic acid and a polyalkyleneglycol or glycol ether, e.g. polyethylene glycol (carbowax), polypropylene glycol, or the corresponding mono-ethers. Thermal stability figures are not given, but these polyoxyalkylene tetrabromo- and tetrachloro-phthalate esters are said, in particular, to possess improved processability in polyphenylene ether resins and resin blends, e.g. blends with other EP resins, particularly vinyl aromatic resins such as polystyrene, styrene-acrylonitrile copolymers, styrene-butadiene copolymers and ABS.

In contrast to the foregoing, and other prior art, and in accordance with the present invention, the tribromoneopentyl esters of ortho-phthalic acid, and especially the ring brominated derivatives, have been found to be unexpectedly advantageous as flame retardants in comparison to other halogenated benzene di- and tricarboxylic acids, e.g. the haloneopentyl esters of tetrabromo- and tetrachloroterephthalic and isophthalic acid disclosed in GB 1341458, and are especially useful as non-dioxin forming flame retardants in acrylonitrile-butadiene-styrene (ABS) rubbers, high impact polystyrene (HIPS) and other engineering plastics (EPs).

Accordingly, the present invention provides novel haloneopentyl esters of the formula

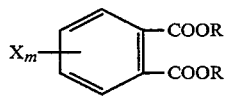

where X is Cl or Br, preferably Br;
m is 0-4, preferably 4; and
each R represents a 2,2-bis(bromomethyl)-3-bromo-n-propyl group, viz a group of the formula

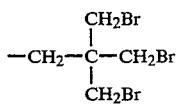

The preferred compound of the invention is the bis ester of tetra-bromo-othophthalic acid, viz. the compound

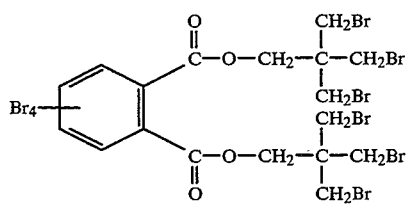

Surprisingly, in view of steric considerations due to the close proximity of so many bromomethyl (—CH₂Br) groups in the end product, the novel compounds of this invention may be readily prepared in high yield by the reaction of tribromoneopentyl alcohol (TBNPA) with the appropriate acid or anhydride, e.g. tetrabromo-orthophthalic acid anhyride, or the corresponding acid chloride. Generally speaking the reaction is conducted under reflux conditions in a water immiscible solvent, such as toluene, with continuous removal of water e.g. by a Dean Stark trap, and in the presence of an esterification catalyst such as $H_2SO_4$, $H_3PO_4$ paratoluene sulphonic acid (PTSA) etc.

TBNPA is obtained by the hydrobromination of pentaerythritol for example, as taught in U.S. Pat. No. 3,932,541, U.S. Pat. No. 3,954,874 and U.S. Pat. No. 4,154,966. The acid reagents, for example tetrabromo-orthophthalic acid anhydride, are either commercially available, or can readily be prepared by bromination or chlorination of the appropriate acid or anhydride.

Whilst this represents the presently preferred method, other routes are available, for example, transesterification reaction of TBNPA with methyl or dimethyl(tetrabromo- or tetrachloro-) orthophthalate. Such esterification reactions are, however, conventional, and the process as such for the manufacture of the novel TBNPA esters of this invention does not form any part of the invention.

In the above formulae, the halogen atoms in the aliphatic side chain need not be the same as those in the aromatic nucleus. Thus the invention contemplate bromo-/chloro- compounds, with bromine in the side chain and chlorine in the aromatic nucleus, as well as the purely brominated compounds containing bromine in both the aromatic nucleus and the side chain.

The preparation of compounds according to this invention is illustrated by the following examples:

EXAMPLE 1

Preparation of bis(tribromoneopentyl)tetrabromo-orthophthalate (BTBNPTBP)

116.1 g of tetrabromophthalic anhydride, 165.1 g of tribromoneopentyl alcohol and 250 ml toluene were mixed in a 500 ml 3-neck round bottomed flask fitted with a stirrer, a temperature probe and a Dean Stark reflux trap. The mixture was heated to reflux temperature and maintained under reflux conditions for 30 minutes to remove any water present via the Dean Stark trap. After 30 minutes the mixture was cooled to 100° C. Concentrated $H_2SO_4$ was then added slowly to the reaction mixture, and the mixture re-heated to reflux temperature. Heating was continued at the reflux temperature, with continuous stirring, for 4 hours, during which time water was collected in the Dean Stark trap.

At the end of the reaction, the reaction mixture was cooled to 20° C., filtered and the filtrate washed with toluene. The wet cake was resuspended in toluene (500 ml) at 55° C., cooled and refiltered at 20° C., the filter cake finally being washed one more time with toluene, and then dried in vacuum at 100° C. for 2 hours.

Products details:
crystalline
m p 267° C.
thermal stability (10% wt loss at a heating rate of 10° C./min)
348° C. analysis C 19.81% (theory 19.71%); H 1.41% (theory 1.46%);
Br 73.0% (theory 72.9%)

The analyses, including n m r not given here, are consistent with the formula hereinbefore given, viz. the compound bis(tribromoneopentyl) tetra-bromo-orthophthalate.

EXAMPLE 2

Preparation of bis(tribromoneopentyl)tetrachloro-orthophthalate

Following the same general reaction procedure as in Example 1, 71.14 g tetrachlorophthalic anhydride was reacted with 165.1 g tribromoneo-pentyl alcohol. Reaction time is 4.5 hours, during which time water is collected in the Dean Stark trap. Product recovery procedure is the same except that the wet filter cake, after washing with toluene, is resuspended in acetone and refiltered before recrystallisation form toluene.

Product details:
crystalline
m p 211° C.
thermal stability (10% wt loss at heating rate of 10° C./min) 342° C.
analysis C 23.67% (theory 23.56%); H 1.57% (theory 1.76%); Br 52.3% (theory 52.3%; Cl 15.3% (theory 15.5%)

The analyses including n m r not given here, are consistent with the formula hereinbefore given, viz. the compound bis(tribromoneopentyl)tetra-chloro orthophthalate.

EXAMPLE 3

Preparation of bis(tribromoneopentyl)orthophthalate

Following the same general procedure as in Example 1, 38.0 g phthalic anhydride was reacted with 116.9 g tribromoneopentyl alcohol in 170 ml toluene. Reaction time was 6 hours following addition of concentrated $H_2SO_4$ during which time water was collected in the Dean Stark trap. At the end of the reaction, the solvent was removed by evaporation and the residue dissolved and then crystallised from 300 ml methanol and filtered. The wet cake was resuspended in 300 ml methanol at 45° C., cooled and re-filtered at 20° C., the filter cake finally being washed with cold methanol, and then dried in vacuum at 70° C. for 2 hours.

Product details:
Crystalline
Melting point 110° C.
Thermal stability (10% wt loss at heating rate of 10° C./min) 310° C.
Elemental analysis C27.94% (theory 27.7%); H 2.41% (theory 2.59%)

As already indicated, the compounds described herein are useful as flame retardant compounds or finishes in or on a variety of substrates.

More particularly they are useful as flame retardant additives in engineering polymers (EPs) such as HIPS, acrylonitrile-butadiene-styrene copolymers (ABS), polystyrene, nylon, transparent polymethylmethacrylate (Perspex) and others. They are also suitable as flame retardants generally in other polymer systems including polyolefins such as polypropylene, polyesters, polyamides and polyurethanes.

In formulating flame retarded compositions according to the invention, the flame retardant esters of this invention will be incorporated into the polymer in any suitable manner to obtain a uniform homogeneous blend. Additional synergistic flame retardant additives may be used in combination with the flame retardant esters, e.g. antimony oxide ($Sb_2O_3$), as well as other optional antioxidants, stabilisers etc. Amounts of flame retardant polyester incorporated into the polymer may range from as little as 0.1% by weight up to 50% by wt. based on the weight of the polymer, preferably from 0.5 to 30% by weight. Where a synergistic flame retardant additive is used, such as antimony oxide, the amount of the flame retardant ester may range from 1 to 20% by wt. preferably 1 to 15% by wt. and the cocomponent e.g. $Sb_2O_3$, from 1 to 20% by wt. preferably 1 to 15 wt %, providing a total content of from 2 to 40 wt % preferably 2 to 30 wt % of both components together.

The utility of the present compounds as flame retardants is illustrated by the following Examples.

EXAMPLES 3 TO 13

The compounds of Examples 1 and 2 compounded into ABS (acrylonitrile-butadiene-styrene, Magnum 3513 from DOW), HIPS (high impact polystyrene, grade 464 from Huntsman) and PP (polypropylene, GWM 203 form lCl) together with antimony oxide in the proportions stated below. Compounding was performed using a torque rheometer at a temperature of 180° C. and a mixing time of 8 minutes. Test specimens of 3.175 mm (⅛") thick were prepared by compression moulding the compounded product at 200° C. (210° C. for PP) and 20×100 kg pressure ($10 \times 10^3$ for PP).

Two small scale flammability tests were used to assess the flame retardancy imparted by inclusion of the additives to the plastics. These were the oxygen index (OI) test, ASTM 2863-87, and the Underwriters Laboratory (UL) subject 94 vertical burn test. In the oxygen index test, the higher the value the greater the flame retardant effect of the additive. In the UL94 test, V-0 is the highest rating for flame retardant effectiveness followed by V-1 and then V-2. "Freely burned" (FB) indicates failure to meet any of these ratings.

| Example No. | Polymer Type | Product of Example 1 % w/w | Product of Example 2 % w/w | Antimony Oxide % w/w | Indicative UL94 (a) | O.I |
|---|---|---|---|---|---|---|
| Control | ABS | — | — | — | FB | 16.8 |
| Control | HIPS | — | — | — | FB | 17.1 |
| Control | PP | — | — | — | FB | 17.4 |
| 3 | ABS | 19.1 | — | 4.6 | V-0 | 26.2 |
| 4 | ABS | 9.6 | — | 4.2 | V-0 | 21.8 |
| 5 | ABS | 9.8 | — | 2.3 | V-2 | 21.5 |
| 6 | ABS | — | 16.0 | 3.9 | V-0 | 23.6 |
| 7 | ABS | — | 7.6 | 1.9 | V-2 | 21.5 |
| 8 | HIPS | 19.1 | — | 4.6 | V-0 | 24.3 |
| 9 | HIPS | — | 19.1 | 4.6 | V-0 | 25.8 |
| 10 | PP | 19.1 | — | 4.6 | V-0 | 25.2 |
| 11 | PP | 16.0 | — | 3.9 | V-2 | 25.8 |
| 12 | PP | — | 19.1 | 4.6 | V-0 | — |
| 13 | PP | — | 16.0 | 3.9 | V-2 | — |

(a) test carried out on a single specimen only.

EXAMPLES 14 TO 16

Using the materials and compounding method of Examples 3-13, test specimens of 1.5875 mm (1/16") thick were prepared by compression moulding. Flame retardancy of the samples were assessed by the OI and UL94 tests.

| Example No. | Polymer Type | Product of Example 1 % w/w | Antimony Oxide % w/w | Indicative UL94 (a) | O.I. |
|---|---|---|---|---|---|
| 14 | ABS | 16.6 | 4.1 | V-0 | 24.9 |
| 15 | ABS | 6.8 | 1.7 | V-2 | — |
| 16 | HIPS | 16.6 | 4.1 | V-0 | 23.7 |

(a) test carried out on single specimen only.

The results from Examples 3–16 clearly demonstrate the flame retardant effectiveness of the additives in the polymer systems studies.

EXAMPLES 17 TO 21

The compound of Example 1 was compounded into ABS using a Baker Perkins MP2030 twin-screw extruder. Test specimens were prepared using an injection-moulder. Comparative specimens containing currently used commercial flame retardant additives, deca-bromodiphenylether (DBDPO) and tetrabromobisphenol-A (TBBPA) were prepared in a similar manner.

Flame retardant effectiveness of the systems was tested using the UL94 vertical burn test. Mechanical properties of the systems were evaluated using the following tests: notched Izod impact (ISO 180/4A), tensile strength (ISO 527), tensile elongation at break (ISO 527), heat distortion temperature at 1.82 MPa (ISO 75), and melt flow index at 22° C. (load 98N to ISO 1133).

The results are tabulated below.

| Test | Example Number | | | | |
|---|---|---|---|---|---|
| | 17 | 18 | 19 | 20 | 21 |
| FR additive type | — | DBDPO | Ex.1 | Ex.1 | TBBPA |
| FR additive content % w/w | — | 13.2 | 15.1 | 15.1 | 18.5 |
| Antimony Oxide % w/w | — | 3.7 | 3.7 | 6.7 | 3.7 |
| Bromine Content % w/w | — | 11.0 | 11.0 | 11.0 | 11.0 |
| Sb:Br ratio (molar) | 0 | 1:5.5 | 1:5.5 | 1:3.0 | 1:5.5 |
| UL94 classification at 1.578 mm (1/16″) | FB | V-0 | V-2 | V-0 | V-2 |
| Notched Izod impact (KJm$^{-2}$) | 30.9 | 12.0 | 14.8 | 8.8 | 11.7 |
| Tensile strength (MPa) | 44.5 | 51.1 | 47.6 | 46.7 | 47.6 |
| Tensile elongation at break (%) | 2.0 | 2.0 | 2.0 | 2.1 | 2.6 |
| Heat distortion temp (°C.) | 83.1 | 72.6 | 77.2 | 76.0 | 81.3 |
| Melt flow index (g/10 min) | 12.8 | 50.2 | 24.4 | 19.2 | 16.0 |

EXAMPLE 22

The test procedure of Examples 3–13 was followed to determine the flame retardant properties of the product of Example 3, viz. bis(tribromoneopentyl) orthophthalate in ABS and HIPS. The results are presented below:

| Polymer Type | Product of Example 2a (% w/w) | Antimony Oxide (% w/w) | Indicative UL94 (a) | O.I. |
|---|---|---|---|---|
| ABS | 16.3 | 3.3 | V-2 | 20.8 |
| HIPS | 16.3 | 3.3 | V-0 | 21.8 |

(a) test carried out on single specimen only.

The above data shows that the compounds of the invention impart good flame retardant and mechanical property characteristics to the polymer blend in comparison with the blends containing materials given the toxicity issues associated with the formation of polybrominated dibenzo-dioxins and -furans when TBBPA and DBDPO are combusted.

We claim:

1. A haloneopentyl esters of the formula

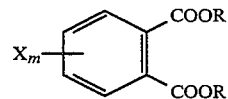

wherein X is Br;

m has a value of 4; and each R is a 2,2-bis(bromomethyl)-3-bromo-n-propyl group.

2. A flame retarded polymer composition, comprising as the flame retardant the ester according to claim 1.

3. A flame retarded polymer composition according to claim 2, wherein the polymer composition further comprises ABS rubber, high impact polystyrene, or engineering plastics materials.

4. A flame retarded composition according to claim 2, in which the flame retardant ester is used in combination with antimony oxide.

5. A method of preparing flame retardant compounds which comprises reacting tribromoneopentyl alcohol with tetrabromo-orthophthalic acid anhydride in a mole ratio of about 2:1 thereby to produce bis-(tribromoneopentyl) tetrabromoorthophthalate.

* * * * *